United States Patent [19]

Barker et al.

[11] Patent Number: 5,745,378
[45] Date of Patent: Apr. 28, 1998

[54] PARAMETER INPUT FOR DRUG DELIVERY PUMP

[75] Inventors: Craig S. Barker, San Carlos; Gordon E. Bell, Walnut Creek, both of Calif.

[73] Assignee: Abbott Laboratories, Abbott Park, Ill.

[21] Appl. No.: 587,098

[22] Filed: Dec. 4, 1995

[51] Int. Cl.$^6$ .................. F04B 49/00; A61M 37/00
[52] U.S. Cl. .......... 364/510; 364/509; 364/237.2; 364/251.2; 345/123; 345/156; 345/168; 345/184; 604/30; 604/67; 604/65; 604/246; 604/260
[58] Field of Search ............... 364/138, 146, 364/152–153, 172, 188, 509–510, 237.2, 237.5, 251, 251.2, 251.1; 604/30, 48, 65–67, 246, 260; 345/104, 123, 156, 168, 173, 184, 183

[56] References Cited

U.S. PATENT DOCUMENTS

| | | | |
|---|---|---|---|
| 4,786,895 | 11/1988 | Castaneda | 345/160 |
| 4,898,578 | 2/1990 | Rubalcaba, Jr. | 604/66 |
| 4,946,439 | 8/1990 | Eggers | 604/67 |
| 5,181,910 | 1/1993 | Scanlon | 604/67 |
| 5,244,463 | 9/1993 | Cordner, Jr. et al. | 604/131 |
| 5,256,157 | 10/1993 | Samiotes et al. | 604/246 |
| 5,366,346 | 11/1994 | Danby | 417/18 |
| 5,368,562 | 11/1994 | Blomquist et al. | 604/65 |
| 5,389,071 | 2/1995 | Kawahara et al. | 604/51 |
| 5,395,321 | 3/1995 | Kawahara et al. | 604/67 |
| 5,442,537 | 8/1995 | Ooji | 363/43 |
| 5,584,671 | 12/1996 | Schweitzer, Jr. et al. | 417/298 |

Primary Examiner—Emanuel T. Voeltz
Assistant Examiner—Tuan Q. Dam
Attorney, Agent, or Firm—Neal D. Marcus

[57] ABSTRACT

Parameters for controlling a drug infusion pump (10) are selected by scrolling through sets of predefined values. A value for either a rate and/or a volume of a fluid to be infused (VTBI) is displayed by pressing a quickset key (38) on a control panel (18) of the pump. Each time that the quickset key is depressed, the value appearing on a display (22) changes to the next value in the corresponding predefined set of values. It is also contemplated that holding the quickset key depressed for at least a predetermined time will cause the display to continuously scroll through successive values from the set of predefined values. The predefined values are selected in the set because they represent the most common values for the parameters used by the pump. An operator can "fine tune" the displayed value to a desired value that is not in the set of predefined values by pressing either a down arrow key (50) or an up arrow control key (52). Using this method and system, the values of the parameters are rapidly entered with minimal chance of error.

15 Claims, 3 Drawing Sheets

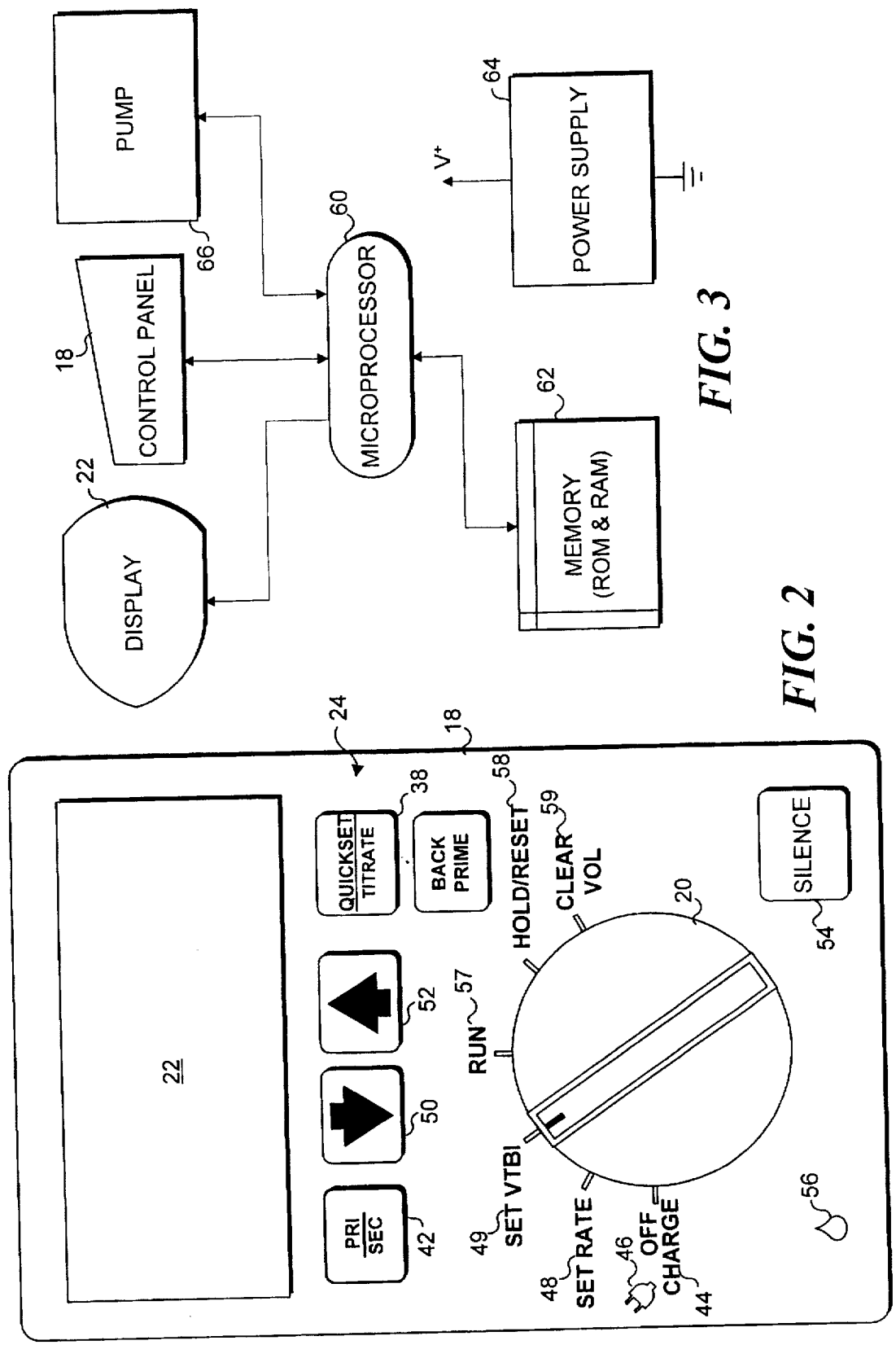

5,745,378

1

PARAMETER INPUT FOR DRUG DELIVERY PUMP

FIELD OF THE INVENTION

This invention generally pertains to a method and system for entering a parameter used to control a pump, and more specifically, entering either a rate of drug infusion, or a volume of drug to be infused.

BACKGROUND OF THE INVENTION

Drug infusion pumps are typically controlled by a microprocessor that is programmed to deliver a specified volume of a drug at a specified rate. The volume and rate are normally selected either by scrolling to a desired value on a display panel or by entering the desired value on a numeric keypad. There are disadvantages to each of these techniques. In the conventional technique for scrolling, the numbers displayed are incremented or decremented and vary by a fixed delta, e.g., 0.1, 1, or 10. Scrolling through numbers on a display to reach a desired value in this manner can be inefficient. For example, if the display starts at 0.0, scrolling by 0.1 increments to a value of 9999 can cause an excessive delay. In consideration of this problem, some control systems enable a faster scroll rate after the scroll control is depressed for a predefined time interval. However, if the scroll rate is increased to allow the operator to reach a desired value more efficiently, it becomes more likely that the numbers on the display will overshoot the desired value, requiring the user to reverse the scroll direction. Thus, although the dual scroll rate helps the user to zero in on a desired value in less time, it will often be necessary to back up to the desired value that was overshot because the high speed scroll rate is too fast to enable the operator to stop when the desired value was displayed.

A numeric keypad clearly provides a much more direct and efficient mechanism for entry of the desired value for a parameter. However, numeric keypads typically include a minimum of from 10 to 12 keys. Such keypads require a relatively large area on a control panel face and contribute to a cluttered layout of the panel. Further, an operator can easily enter an erroneous value for a parameter using a keypad, by accidentally pressing an unintended key or by pressing an incorrect sequence of keys. Simply reversing two digits of a keypad entry can potentially cause harm to a patient if the value entered causes a drug infusion pump to administer too large a volume of drug or to administer the drug too rapidly.

It has been noted that most drugs are infused at only a few defined rates and in only a few defined volumes. Accordingly, it would be desirable to employ an efficient scheme for entering rate and volume parameters that is based on this fact and which does not require that a numeric keypad be provided on the control panel of the drug pump. Selecting a desired value from among a limited set of values commonly employed for the drug delivery rate and volume should also help to minimize errors that can arise when these parameters are entered using a conventional scrolling technique or by entry on a numeric keypad.

SUMMARY OF THE INVENTION

In accordance with the present invention, a method is defined for input of a parameter used to control a medical device. The method includes the step of defining a set of values for the parameter. The values in this set increase in unequal increments and are selected based upon a frequency of use of the values in controlling the medical device. Thus, the specific values in the set are used substantially more often than other values that are not included in the set. A quick entry control is provided on the medical device. When actuated by an operator, the quick entry control scrolls through the set of values, displaying successive values from the set in sequence. A value that is last displayed is employed as the parameter used to control the medical device.

The method further comprises the step of providing a control that enables the operator to select a value for the parameter that is not included in the set of values. This aspect of the method enables the operator to "fine tune" or change the value from the set that was previously entered for the parameter to the desired value, if the desired value is different than any value in the set.

In the preferred embodiment, the medical device comprises a drug pump, and the parameter comprises a rate of a drug infusion. The parameter may also comprise a volume of a drug to be infused.

The method further comprises the step of defining a different set of values for a different parameter used to control the medical device. The values of the different set increase in unequal increments and are selected based upon a frequency with which such values are used in controlling the medical device; the different set of values are used substantially more often than other values not included in the different set. The quick entry control on the medical device, when actuated by the operator, scrolls through the different set of values, displaying successive values from the different set in sequence. A value that is last displayed from the different set of values is employed as the different parameter used to control the medical device. In this case, the parameter comprises a rate of a drug infusion, and the different parameter comprises a volume of a drug to be infused.

Another step of the method provides an entry mode control for selecting either the parameter or the different parameter that are to be entered by the operator. The quick entry control scrolls through the set of parameters when the entry mode control is set to select the entry of the parameter and scrolls through the different set of parameters when the entry mode control is set to select entry of the different parameter.

Another aspect of the present invention is directed to a control for a medical device that enables entry of a parameter used to control the medical device. The control comprises a microprocessor programmed to respond to the parameter entered by an operator to control the medical device using the parameter. A memory, which is coupled to the microprocessor, stores a program executed by the microprocessor to control the medical device and stores a set of values for the parameter. The values increase in unequal increments and are selected based upon a frequency of their use in controlling the medical device. The set of values are used substantially more often than other values not included in the set. A control panel is provided that includes a quick entry control, which when actuated by the operator, scrolls through the set of values. Values for the parameter appear on a display as the operator scrolls through the values. The last value thus displayed is used by the microprocessor for the parameter employed in controlling the medical device.

Other functions of the control are generally consistent with the steps of the method described above.

BRIEF DESCRIPTION OF THE DRAWINGS FIGURES

The foregoing aspects and many of the attendant advantages of this invention will become more readily appreciated as the same becomes better understood by reference to the following detailed description, when taken in conjunction with the accompanying drawings, wherein:

FIG. 2 is an enlarged view of a control panel for the drug infusion pump of FIG. 1;

FIG. 3 is a schematic block diagram of functional components of the drug infusion pump.

DESCRIPTION OF THE PREFERRED EMBODIMENT

Figure 1:
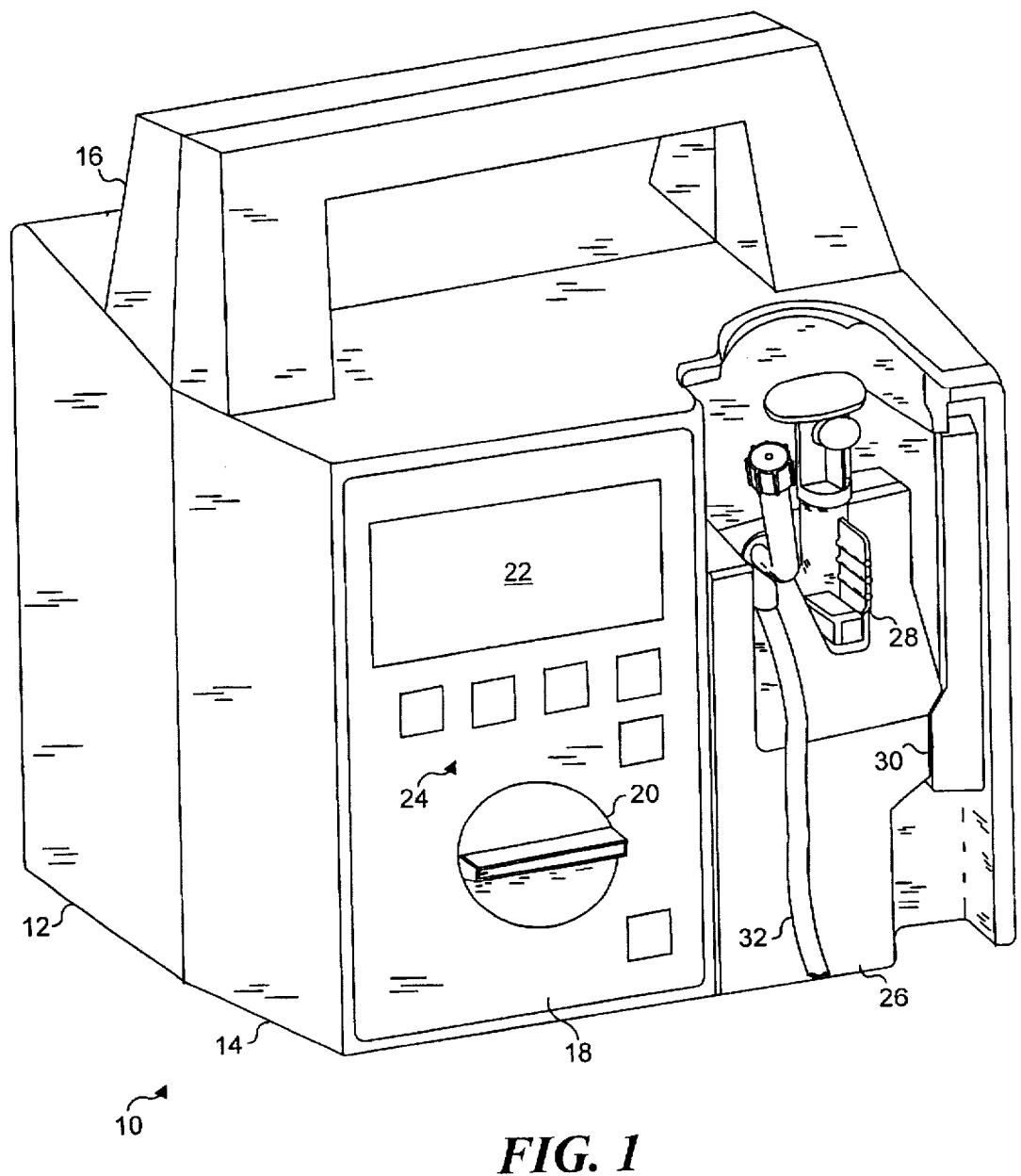
FIG. 1 is an isometric view of a cassette drug infusion pump in which the present invention is employed.

FIG. 1 illustrates a cassette-type drug infusion pump 10, which is employed for infusing a drug into a patient from a primary and/or a secondary drug reservoir (not shown). Drug infusion pump 10 is intended to be exemplary of many such pumps with which the present invention might be used. The pump is enclosed within a plastic molded clamshell housing, including a back section 12 and a front section 14. The housing sections include a handle 16 for carrying pump 10.

A front control panel 18 on the pump includes a knob 20 which is rotated to different positions to select operating conditions of the pump. Alphanumeric data and messages are presented on a display 22, which in the preferred embodiment comprises a multi-line liquid crystal display (LCD). The alphanumeric messages include text for prompting an operator in entering parameters used to control the pump, messages indicating the condition of the pump and status of the pumping process, and messages describing alarm conditions that may arise from time to time if an abnormal or undesired event, e.g., detection of air bubbles, occurs during the infusion of fluid into a patient.

Immediately below display 22 is a keypad 24 that is used for entry of data and for selecting options that control the pump. Some of the keys on keypad 24 perform multiple functions; the function that is activated by depressing the key depends upon the operating condition selected by an operator with knob 20. Control panel 18 is generally water resistant, being covered by a continuous transparent membrane (not separately indicated), except where knob 20 is disposed.

To the right of control panel 18 is a hinged door 26, which is opened for insertion of a disposable pumping cassette 28 by lifting a handle 30. The design of pumping cassette 28 and details concerning it are not shown, since they are not relevant to the present invention. When hinged door 26 is closed with pumping cassette 28 positioned behind it, the cassette is latched in place so that it can be actuated by the pumping mechanism of pump 10. Actuation of pumping cassette 28 by pump 10 causes fluid to flow to a patient through a flexible line 32.

In FIG. 2, details of control panel 18 are shown that are relevant to entry of values for parameters used in controlling the pump to deliver a drug or other medicinal fluid. Among the details shown are the various positions to which knob 20 can be set. In a position 44 labeled "OFF/CHARGE," the pump is stopped, and an internal battery (not shown) is charged when the pump is connected to alternating current (AC) power. While the internal battery of pump 10 is being charged, an icon 46, which is shaped like an AC line plug, is lighted, indicating that the pump is energized from the AC source.

A position 48 labeled "SET RATE" is selected to enable the operator to enter the delivery rate parameters for the PRIMARY or SECONDARY channels. Display 22 prompts the operator to enter the value. When a key 42 labeled "PRI/SEC" is activated, the operator prompt on display 22 changes between PRIMARY and SECONDARY. This position is selected when it is necessary to enter or change a delivery rate, for example, to infuse a different drug.

A position 49 labeled "SET VTBI" is selected with knob 20 to enable the operator to enter the Volume To Be Infused (VTBI) parameters for the PRIMARY or SECONDARY channels. Display 22 prompts the operator to enter the value. When key 42 labeled "PRI/SEC" is activated, the operator prompt on display 22 changes between PRIMARY and SECONDARY. This position is selected when it is necessary to enter or change a volume, for example, to repeat a dose. If the operator enters parameters for only one of the two fluids (primary or secondary), the pump does not attempt to infuse the other. Pump 10 thus operates in a primary only mode in which only the primary fluid is delivered, a secondary only mode in which only the secondary fluid is delivered, and in a piggyback mode. In the piggyback mode, the secondary fluid is delivered at a selected rate until the desired VTBI that was previously entered for the secondary fluid has been achieved. At this point, the pump begins delivery of the primary fluid at the rate that was entered by the operator. When the pump switches over to delivery of the primary fluid, an audible alarm sounds for a brief period of time. This and other audible alarms are silenced by depressing a control key 54 (labeled "SILENCE"). After the primary VTBI has been delivered, a VTBI Complete alarm sounds and the pump switches to a keep vein open (KVO) mode, in which only a minimum amount of fluid necessary to prevent collapse of a vein is delivered.

The rate and the VTBI for a drug or medicinal fluid (either the primary and/or secondary fluids) are normally entered by an operator using the present invention, prior to starting the drug or medicinal fluid infusion. The present invention is used for entering the rate and VTBI of drugs and medicinal fluids, for controlling the operation of the pump in each of the three modes described above. Thus, the rate and VTBI for a primary fluid, a secondary fluid, or both fluids may be entered by an operator using the present invention.

When the knob is in SET RATE position 48, the operator is prompted to enter the primary or secondary rate. In response to a prompt to enter the rate that appears on display 22 in a SET RATE mode, the operator can quickly enter a desired rate by repetitively pressing a QUICKSET/TITRATE key 38. (This key will be hereafter be referred to throughout the remainder of the Disclosure as quickset key 38.) Each time that quickset key 38 is pressed, a successively greater value in a sequence of predefined rate values appears on display 22; and if quickset key 38 is pressed when the maximum value for rate in the sequence is displayed, the value scrolls around to display the first value in the set of predefined values for rate.

In the preferred embodiment, the sequence in the set of values predefined for rate is as follows: 0.0, 5.0, 25.0, 30.0, 50.0, 75.0, 100, 125, 150, 200, 500, and 999. The predefined values in this set correspond to the most common rates used for infusing medicinal fluids and drugs, for the majority of patients. However, if the operator needs to select a value for rate that differs from any of these predefined values, it is expedient to quickly scroll to the nearest predefined value in this set of values by repetitively pressing quickset key 38. Alternatively, although not currently implemented, it is contemplated that the current preferred embodiment of the present invention can readily be modified to enable the operator to quickly scroll through the predefined values in the set by holding the quickset key in a depressed state. Holding quickset key 38 depressed for more than one second would then cause the value for rate in display 2p (from the set of predefined values) to increment continuously at a speed sufficiently slow so that the operator could easily stop on a desired one of the predefined values in the set by releasing the quickset key. Once the closest predefined value for rate from the set is thus obtained in display 22, the operator can press either a down arrow key 50 or an up arrow key 52 to decrement or increment the displayed value for rate until the desired value is obtained. Keeping either the up or down arrow key depressed will cause a continuous increment or decrement, respectively, of the value in display 22.

When the knob is in SET VTBI position 49, the operator is prompted to enter the primary or secondary VTBI. In response to a prompt to enter the VTBI that appears in display 22 in a SET VTBI mode, the operator can again repetitively press quickset key 38 to cause the display to scroll through a set of predefined values for VTBI. The set of values for VTBI in sequence is as follows: 0.0, 10.0, 25.0, 50.0, 100, 150, 250, 500, 1000, 2000, 3000, 4000, and 9999. The values in this predefined set were selected based on the frequency of their use; they represent the most common values for VTBI for different types of medicinal fluids and drugs likely to be infused using pump 10. Instead of repetitively pressing the quickset key to scroll through the values, it is also contemplated that the preferred embodiment can be modified so that holding quickset key 38 depressed for more than one second will cause the predefined set of values to scroll on the display, sufficiently slowly to enable the operator to stop at a desired value If the desired value for VTBI is not among the predefined set of such values, the operator can quickly scroll to the nearest one of the predefined values in the set for VTBI, and then using down arrow key 50 or up arrow key 52 as described above, can decrement or increment the displayed value to achieve the desired value for VTBI.

After the values for the parameters used to infuse the primary and secondary fluids are thus entered, knob 20 is rotated to a RUN position 57, causing the pump to enter a RUN condition in which one of the medicinal fluids or drugs is infused using the rate and VTBI values entered by the operator. If one of the settings has not yet been entered, display 22 will prompt the operator to enter the omitted parameter. When fluid is infused into the patient, an LED "drop" icon 56 is repetitively briefly energized and deenergized, causing the icon to blink.

It should be noted that the specific values used in the sets of predefined values for rate and VTBI can readily be changed within software that controls the pump operation. It is expected that for different types of pumps and for different types of medicinal fluids and drugs that are infused, the optimum choice of predefined values might differ. A considerable variation in the predefined values and in the number of such values that are selected for each set will not adversely impact the benefits of the present invention. Furthermore, other changes, such as decrementing the predefined values starting with a maximum predefined value, will not materially change the benefits of the invention and are certainly contemplated.

Rotating knob 20 to a HOLD/RESET position 58 causes delivery of fluid by the pump to be suspended. If an alarm condition prompted the operator to select the HOLD/RESET position, the audible alarm is silenced when HOLD/RESET position 58 is selected with the knob.

Rotating knob 20 to a CLEAR VOLUME position 59 causes the total volume infused for both the primary and secondary fluids to be cleared from display 22. However, prior to clearing the display, a CLEAR TOTAL VOLUME audible alarm sounds, enabling the operator to rotate knob 20 away from the CLEAR VOLUME position in time to prevent consequences of an inadvertent selection of this position.

FIG. 3 illustrates the functional components of pump 10. Control of pump 10 is implemented using a microprocessor 60, which is coupled to various components of the pump. For example, microprocessor 60 produces signals that control the alphanumeric messages appearing on display 22. Control panel 18 is bidirectionally coupled to microprocessor 60 so that depression of the keys on the keypad is detected by the microprocessor. In addition, the microprocessor provides the signals that energize the visual icons and audible alarms used on the operator interface. Operation of a pumping mechanism 66 that is used for actuating the disposable cassette is controlled by microprocessor 60. The coupling to the pumping mechanism is bidirectional, so that microprocessor 60 receives signals from an air-in-line sensor and other sensors of pumping mechanism 66 (none shown).

Machine language instructions comprising the software that controls the operation of the pump, causing it to respond to the values of the parameters entered by an operator are stored in a memory 62 that includes both read only memory (ROM) and random access memory (RAM). Values for the parameters entered by the operator are stored in RAM, whereas the machine instructions controlling the basic operation of microprocessor 60 are stored in ROM. A power supply 64 provides one or more voltages suitable for energizing the components of pump 10.

Figure 4:
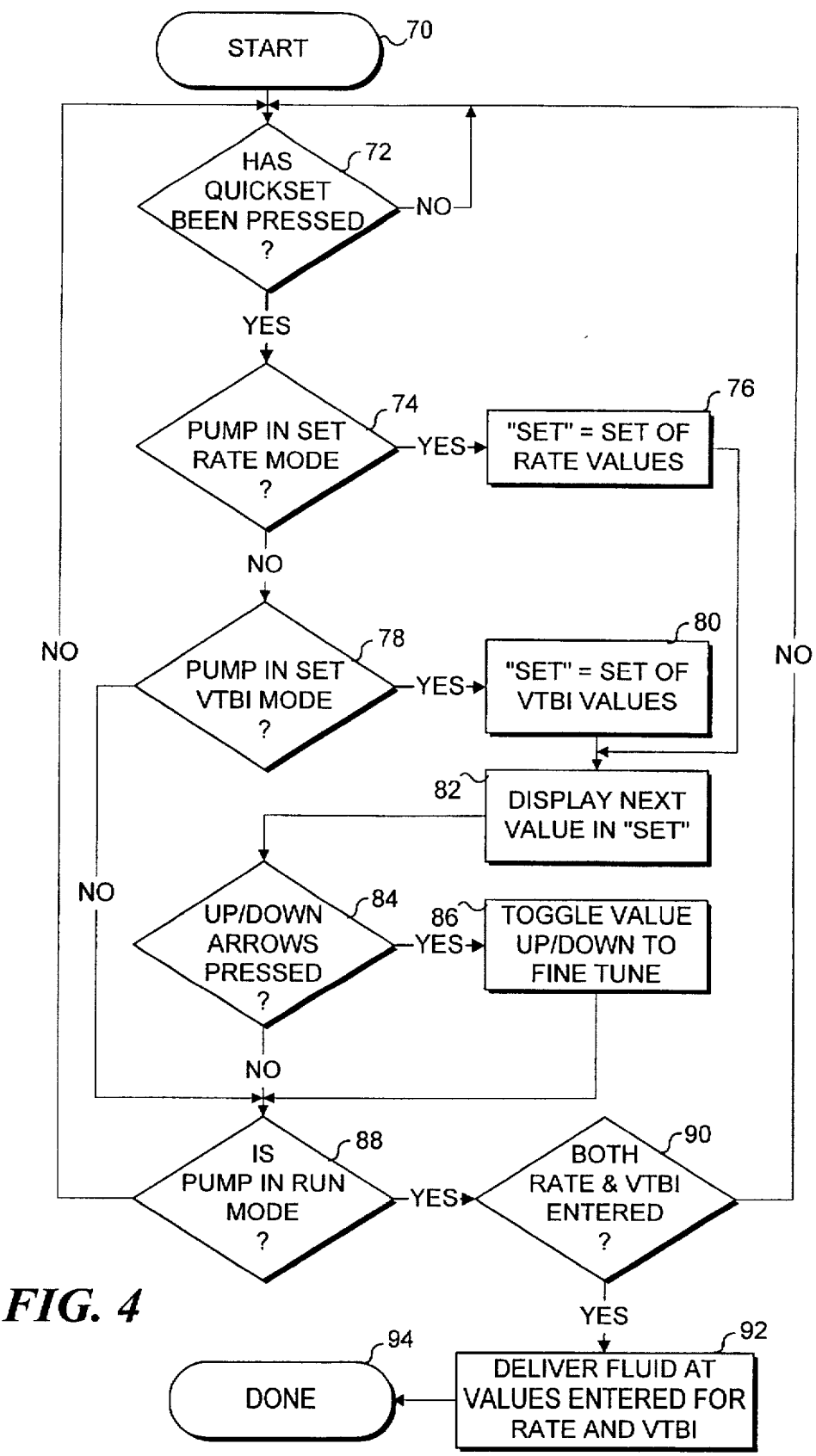
FIG. 4 is a flow chart showing the logical steps implemented when executing the present invention to enter parameters used to control the drug infusion pump.

In FIG. 4, a flow chart illustrating the logical steps involved in implementing the present invention is shown. Beginning at a start block 70, the logic proceeds to a decision block 72 that determines if the quickset key on control panel 18 has been pressed. If not, the flow chart of FIG. 4 indicates that the logic loops back to wait until the quickset key is pressed. In fact, the logic does not actually loop in this manner. Pressing the quickset key generates an interrupt that initiates the remaining steps of the flow chart. The loop shown in connection with decision block 72 is merely a simplistic way to show that the control logic reacts to the operator pressing quickset key 38.

After quickset key 38 has been pressed, a decision block 74 determines if the pump is in the SET RATE mode. If so, the logic proceeds to a block 76 in which the value for a flag SET is selected to indicate that the set of predefined values for rate is to be used (rather than the set of predefined values for VTBI). Thereafter, the logic proceeds to a block 82. However, if the pump is not in the SET RATE mode, the logic proceeds to a decision block 78 to determine if the pump is in the SET VTBI mode. If so, a block 80 provides for making the value for the flag SET indicate that the set of predefined values for VTBI should be used. Thereafter, the logic also proceeds to block 82.

In block 82, the logic displays the next value from the set of values indicated by the flag SET. If entering block 82 from block 76, the next value displayed will be from the predefined set values for rate. If entering block 82 from block 80, the next value displayed will be from the predefined set of values for VTBI.

From block 82, the logic proceeds to a decision block 84. In this decision block, the logic determines if either the up or down arrow key has been pressed. If so, a block 86 toggles the value in display 22 up or down, depending upon which arrow key was pressed, to fine tune the value in display 22 to the desired value. This step enables the operator to select a value for either rate or VTBI that is not among the predefined values in the set of such values, by scrolling to the desired value using the up or down arrow key on the control panel.

Referring back to decision block 78, a negative response to the inquiry indicating that the pump is not in the SET VTBI mode leads to a decision block 88. This point is also reached following block 86. In decision block 88, the logic determines if the pump is in the REIN mode. If not, the logic returns back to decision block 72, enabling further presses of the quickset key to increment the display to the next predefined value for either the set of predefined rate values, or the set of predefined VTBI values. A positive response to decision block 88 leads to a decision block 90. In this decision block, the logic determines if both the rate and VTBI parameters have been entered. If so, a block 92 begins delivering the medicinal fluid or drug in accordance with the values entered for rate and VTBI. A negative response to decision block 90 leads back to decision block 72, so that the operator can enter the omitted parameter. After block 92, the logic terminates in a block 94.

The present invention thus enables an operator to quickly select a desired value from among predefined values for rate and VTBI that are commonly used. Since only the more commonly used values are included within the sets of predefined values for these parameters, it is unlikely that the operator will make an error in entering values for these parameters. Furthermore, the values entered for the parameters can be selected rapidly, without the time delay involved in scrolling to the values that would be incurred using only the up or down arrow keys.

Although the present invention has been described in connection with the preferred form of practicing it, those of ordinary skill in the art will understand that many modifications can be made thereto within the scope of the claims that follow. For example, the present invention has been disclosed in connection only with setting rate and VTBI parameters on a drug infusion pump; however, it will be apparent that other types of parameters and data can be entered on other types of medical devices using the present invention. Accordingly, it is not intended that the scope of the invention in any way be limited by the above description, but instead be determined entirely by reference to the claims that follow.

The invention in which an exclusive right is claimed is defined by the following:

1. A method for input of a desired value for a parameter used to control a medical device, comprising the steps of:
   (a) defining a set of values for said parameter, said values increasing in unequal increments and being selected for inclusion in the set based upon a frequency of use in controlling the medical device, said values in said set being used substantially more often than other values not included in the set;
   (b) providing a dedicated quick entry control on the medical device that when actuated by an operator scrolls through said set of values displaying successive values from said set, said successive values that are displayed being independent of a rate at which said quick entry control is actuated by the operator; and
   (c) employing a value that is displayed for the parameter, for use in controlling the medical device.

2. The method of claim 1, further comprising the step of providing a control that enables the operator to select a value for the parameter that is not included in said set of values.

3. The method of claim 1, wherein the medical device comprises a pump, and the parameter comprises a rate at which a fluid will be pumped.

4. The method of claim 1, wherein the medical device comprises a pump, and the parameter comprises a volume of a fluid to be pumped.

5. The method of claim 1, further comprising the steps of:
   (a) defining a different set of values for a different parameter used to control the medical device, said values of said different set increasing in unequal increments and being selected based upon a frequency of use in controlling the medical device, said different set of values being used substantially more often than other values not included in the different set;
   (b) providing the quick entry control on the medical device that when actuated by the operator scrolls through said different set of values, displaying successive values from said different set in sequence; and
   (c) employing a value that is displayed, for the different parameter used to control the medical device.

6. The method of claim 5, wherein the medical device comprises a pump, and wherein the parameter comprises a rate at which a fluid is pumped, and the different parameter comprises a volume of the fluid to be pumped.

7. The method of claim 5, further comprising the step of providing an entry mode control for selecting one of the parameter and the different parameter to be entered by the operator, wherein the quick entry control scrolls through the set of predefined values for the parameter when the entry mode control is set to select entry of a value for the parameter and scrolls through the different set of values for the different parameter when the entry mode control is set to select entry of a value for said different parameter.

8. A control for a medical device that enables entry of a desired value for a parameter used to control the medical device, comprising:
   (a) a microprocessor programmed to respond to the desired value of the parameter entered by an operator to control the medical device;
   (b) a memory, which is coupled to the microprocessor, for storing a program executed by the microprocessor to control the medical device, and for storing a set of predefined values for the parameter, said predefined values increasing in unequal increments and being selected based upon a frequency of use in controlling the medical device, said set of predefined values being used for the parameter controlling the medical device substantially more often than other values that are not included in the set;
   (c) a control panel that includes a dedicated quick entry control, which when actuated by the operator, scrolls through the set of values; and
   (d) a display for displaying successive values for the parameter as the operator scrolls through the predefined values, said successive values that are displayed being independent of a rate at which the operator actuates said quick entry control, a value displayed being used by the microprocessor for the parameter used in controlling the medical device.

9. The control of claim 8, wherein the control panel includes a control that enables the operator to select a specific value for the parameter that is different than any value in the set of predefined values, said specific value being displayed on the display and being employed for the parameter used in controlling the medical device.

10. The control of claim 8, wherein the medical device is a pump, and the parameter comprises a rate at which a fluid is pumped.

11. The control of claim 8, wherein the medical device is a pump, and the parameter comprises a volume of a fluid to be pumped.

12. The control of claim 8, wherein a different parameter is also used by the microprocessor for controlling the medical device, and wherein said memory is also used for storing a different set of predefined values for said different parameter, said predefined values of said different set increasing in unequal increments and being selected based upon a frequency of use in controlling the medical device, said different set of predefined values being used substantially more often than other values that are not included in the different set.

13. The control of claim 12, wherein the quick entry control is used to scroll through the different set of predefined values, and wherein a value displayed on the display is employed as the different parameter used for controlling the medical device.

14. The control of claim 13, wherein the control panel includes an entry mode control enabling the operator to select the desired value for entry of one of the parameter and the different parameter.

15. The control of claim 13, wherein the medical device comprises a pump, and wherein the parameter comprises a rate at which a fluid is pumped, and the different parameter comprises a volume of fluid to be pumped.

* * * * *